US006303564B1

(12) United States Patent
Littau et al.

(10) Patent No.: US 6,303,564 B1
(45) Date of Patent: Oct. 16, 2001

(54) DETERGENTS, CLEANING COMPOSITIONS AND DISINFECTANTS COMPRISING CHLORINE-ACTIVE SUBSTANCES AND FATTY ACID ALKYL ESTER ETHOXYLATES

(75) Inventors: Cheryl Ann Littau, Liederbach; Ignaz Wimmer, Winhöring, both of (DE)

(73) Assignee: Clariant GmbH, Frankfurt (DE)

( * ) Notice: Subject to any disclaimer, the term of this patent is extended or adjusted under 35 U.S.C. 154(b) by 0 days.

(21) Appl. No.: 09/203,428

(22) Filed: Dec. 1, 1998

(30) Foreign Application Priority Data

Dec. 2, 1997 (DE) ............................... 197 53 316

(51) Int. Cl.[7] ............................... C11D 9/26; C11D 1/12; C11D 3/395
(52) U.S. Cl. .................. 510/505; 510/379; 510/302; 510/421; 510/424; 510/367
(58) Field of Search .................... 510/506, 505, 510/488, 491, 379–381, 302, 421, 424, 367

(56) References Cited

U.S. PATENT DOCUMENTS

| | | | |
|---|---|---|---|
| 3,762,859 | * 10/1973 | Wixon et al. | 8/18 |
| 4,022,808 | * 5/1977 | Yoshihara et al. | 260/410.6 |
| 4,188,305 | 2/1980 | Halas . | |
| 4,368,267 | 1/1983 | Hou et al. . | |
| 4,555,349 | * 11/1985 | Butterworth et al. | 252/8.6 |
| 4,774,079 | * 9/1988 | Shin et al. | 424/66 |
| 4,840,942 | * 6/1989 | Iwasaki et al. | 514/120 |
| 5,288,423 | * 2/1994 | Behan et al. | 252/174.11 |
| 5,374,750 | * 12/1994 | Nakamura et al. | 554/149 |
| 5,554,315 | * 9/1996 | Tonomura et al. | 510/535 |
| 5,749,977 | * 5/1998 | Lallier et al. | 134/40 |
| 5,759,988 | * 6/1998 | Heile et al. | 510/441 |
| 5,905,102 | * 5/1999 | Nagasawa et al. | 523/161 |

FOREIGN PATENT DOCUMENTS

| | | |
|---|---|---|
| 2915108 | 10/1979 | (DE) . |
| 3008174 | 9/1981 | (DE) . |
| 19514413 | 10/1995 | (DE) . |
| 0335295 | 10/1989 | (EP) . |
| 0636690 | 2/1995 | (EP) . |
| 227119 | 2/1926 | (GB) . |
| 2288600 | 10/1995 | (GB) . |
| 0 629 671 | * 7/1996 | (JP) . |

OTHER PUBLICATIONS

European Search Report.
XP 000659303 "Methyl Ester Ethoxylates" Michael F. Cox and Upali Weerasooriya, Journal of The American Oil Chemists' Society, vol. 74, No. 7, Jul. 1, 1997, pp. 847–859.
XP–000778430 "Optimization of Surfactant Systems Containing Methyl Ester Ethoxylates," C. Littau, D. Miller, SÖFW–Journal Seifen, Oele, Fette, Wachse, vol. 124, No. 11, 11/98 pp. 690, 692, 694, 696.
Derwent Patent Family Report and/or Abstracts.

* cited by examiner

Primary Examiner—Cynthia H. Kelly
Assistant Examiner—Dawn L. Garrett
(74) Attorney, Agent, or Firm—Susan S. Jackson; Scott E. Hanf

(57) ABSTRACT

Detergents, cleaning compositions and disinfectants comprising a chlorine-active substances and fatty acid alkyl ester ethoxylates Detergents, cleaning compositions and disinfectants comprising a chlorine-active substance and a fatty acid alkyl ester ethoxylate of the formula $$RO(CH_2CH_2O)_nCOR^1$$

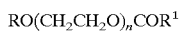

in which R is $C_1$–$C_4$-alkyl, $R^1$ is $C_5$–$C_{22}$-alkyl or $C_5$–$C_{22}$-alkenyl, and n is a number from 1 to 30.

4 Claims, No Drawings

DETERGENTS, CLEANING COMPOSITIONS AND DISINFECTANTS COMPRISING CHLORINE-ACTIVE SUBSTANCES AND FATTY ACID ALKYL ESTER ETHOXYLATES

DESCRIPTION OF THE RELATED ART

In America, Japan and other regions where washing machines do not generally have active heating systems, chlorine-active substances, in particular sodium hypochlorite, are used for bleaching and disinfecting. The sodium hypochlorite solution displays its full bleaching effect at temperatures as low as 20° C. Effective oxidizing agents here may, firstly, be the hypochlorous acid and its anion, or, secondly, the atomic oxygen formed during degradation of the acids. A disadvantage is that sodium hypochlorite solutions are incompatible with many other detergent ingredients, meaning that the bleaching agent must be added separately.

This is true particularly in the case of nonionic surfactants. Thus, the hydroxyl groups of fatty alcohol ethoxylates, for example, are already oxidized at temperatures of 40° C. and above within a short time in the presence of hypochlorite.

EP Patent 636690 describes a gelatinous cleaning composition comprising hypochlorite and an acrylic polymer for stabilizing the surfactants. The stabilization of cleaning compositions comprising hypochlorite using water-soluble sulfo polymers is described in GB-A-227119.

SUMMARY OF THE INVENTION

The object of the invention was to provide nonionic surfactants which are stable toward hypochlorite, are readily biodegradable and well tolerated by the skin. This object is achieved by the use of the fatty acid alkyl ester ethoxylates described below.

The invention provides detergents, cleaning compositions and disinfectants which, in addition to the chlorine-active substance, comprise a fatty acid alkyl ester ethoxylate of the formula $$RO(CH_2CH_2O)_nCOR^1$$

where R is $C_1$–$C_4$-alkyl, $R^1$ is $C_5$–$C_{22}$-alkyl or $C_5$–$C_{22}$-alkenyl, and n is a number from 1 to 30.

DESCRIPTION OF THE PREFERRED EMBODIMENTS

These fatty acid alkyl ester ethoxylates are prepared by known processes by reacting ethylene oxide and the fatty acid ester in the presence of a catalyst (U.S. Pat. No. 4 022 808; DE-A-2915108, DE-A-30 08 174; EP-A-335 295; U.S. Pat. No. 5,374,750). Preferred fatty acid alkyl esters are the methyl esters, and preferred parent fatty acids are saturated and unsaturated $C_{12}$–$C_{18}$-fatty acids, in particular the naturally occurring fatty acids or fatty acid mixtures, such as lauric, stearic or oleic acid, or tallow fatty acid or coconut fatty acid.

The detergents, cleaning compositions and disinfectants according to the invention, which may be solid or liquid, generally comprise from 0.1 to 15% by weight, preferably from 0.2 to 10% by weight, in particular from 2 to 6% by weight, of the chlorine-active substance. The most important of these chlorine-active substances are the hypochlorites, in particular sodium hypochlorite. Other chlorine-active substances are dichloroisocyanurates, trichlorocyanuric acid, N-chlorinated succinimides, malonimides, phthalimides or naphthalimides, dichlorodimethylhydantoin, N-chlorosulfonamide and chloramines. The amount of fatty acid alkyl ester ethoxylate in the detergents, cleaning compositions and disinfectants according to the invention is from 0.2 to 20% by weight, preferably from 0.5 to 10% by weight, in particular from 0.3 to 5% by weight. It has proven advantageous to use the fatty acid alkyl ester ethoxylates together with secondary alkanesulfonates (SAS). This combination also improves the stability of the hypochlorite-surfactant system. These sec. alkanesulfonates are used in amounts such that the weight ratio of fatty acid alkyl ester ethoxylate to alkanesulfonate is from 4:1 to 1:4, preferably from 2:1 to 1:2, in particular 1:1.

Depending on the intended use, the detergents, cleaning compositions and disinfectants according to the invention may also comprise other anionic, nonionic, cationic and/or amphoteric cosurfactants, provided that these cosurfactants are not attacked by the chlorine-active substance.

Typical examples of such cosurfactants are amine oxides, betaines, sarcosinates, taurates, alkylsulfates, alkylsulfonates, alkylarylsulfonates, alkylphenol ether sulfates, phosphoric acid alkyl esters, sulfoxides, phosphorus oxides, alkyldiphenyl oxide sulfonates and soaps.

The detergents, cleaning compositions and disinfectants according to the invention are, for example, detergents, disinfectants, disinfecting cleaning compositions, all-purpose cleaners, sanitary cleaners, bath cleaners and automatic dishwashing detergents. Depending on the intended use, in addition to said surfactants, they may also comprise the specific auxiliaries and additives in each case, for example builders, foam inhibitors, salts, bleaching agents, bleach activators, optical brighteners, antiredeposition agents, solubilizers, enzymes, thickeners, preservatives, perfumes and dyes, pearlizing agents, emulsifiers, superfatting agents, biogenic active ingredients (plant extracts and vitamin complexes), and sequestering agents.

EXAMPLES

EXAMPLE 1

Cleaner Comprising Sodium Hypochlorite, Clear, Liquid

| Composition (% by weight) | 100% |
|---|---|
| Deionized water | ad 100% |
| Fatty acid alkyl ester ethoxylate (Clariant) | 0.90 |
| Hostapur ® SAS 30 (Clariant) | 1.50 |
| Sodium hydroxide | 1.00 |
| Sodium hypochlorite (15% strength) | 3.75 |
| Perfume oil | |

EXAMPLE 2

Sanitary Cleaner Containing Sodium Hypochlorite, Cloudy, Liquid

| Composition (% by weight) | 100% |
|---|---|
| Deionized water | ad 100% |
| Fatty acid alkyl ester ethoxylate (Clariant) | 1.00 |
| Hostapur ® SAS 30 (Clariant) | 0.75 |
| Sodium hydroxide | 1.00 |
| Sodium hypochlorite (15% strength) | 7.50 |

Preparation:

The components are stirred together well in the order given.

Chemical Name of the Commercial Products:
  Hostapur® SAS 30: secondary $C_{13}$–$C_{17}$-alkanesulfonate, sodium salt
  Fatty acid alkyl ester ethoxylate: $C_6$–$C_{10}$-alkyl fatty acid methyl ester ethoxylate containing 9 mol of EO Determination of the Stability of Sodium Hypochlorite in Combination with Surfactants In accordance with the ASTM D2022 method, the chloride content of an aqueous solution comprising 1% surfactant, 4.5% $NaClO_4$ and 0.3% NaOH was measured. The samples were stored at 40° C., and the chloride content was measured in each case after 10, 20, 30 and 70 days. The results are given in the table below.

|      | Surfactant | | | | |
| ---- | --- | --- | --- | --- | --- |
| Days | 1 | 2 | 3 | 4 | 5 |
| 10 | 68 | 88 | 92 | 88 | 95 |
| 20 | 0 | 72 | 80 | 80 | 80 |
| 30 | 0 | 60 | 70 | 73 | 72 |
| 70 | 0 | 0 | 0 | 60 | 58 |

The following surfactants or surfactant mixtures were tested:
1. $C_{11}$-oxo alcohol polyglycol ether containing 7 mol of EO
2. $C_6/C_{10}$-alkyl fatty acid methyl ester ethoxylate containing 9 mol of EO
3. $C_{12}/C_{14}$-alkyl fatty acid methyl ester ethoxylate containing 12.5 mol of EO
4. sec. alkanesulfonate, Na salt
5. 1:1 mixture of $C_6/C_{10}$-alkyl fatty acid methyl ester ethoxylate containing 9 mol of EO and sec. alkanesulfonate The values given in the table indicate the active chlorine content in %, based on the starting value.

This table shows that the fatty acid methyl ester ethoxylate alone or together with a sec. alkanesulfonate ensures sufficiently long stability in a mixture with hypochlorite.

What is claimed is:

1. A detergent, cleaning composition or disinfectant comprising a chlorine-active substance, a fatty acid alkyl ester ethoxylate of formula $$RO(CH_2CH_2O)_nCOR^1$$

which R is $C_1$–$C_4$-alkyl, $R^1$ is $C_5$–$C_{22}$-alkyl or $C_5$–$C_{22}$-alkenyl, and n is a number from 1 to 30, a secondary alkanesulfonate and at least one auxiliary selected from the group consisting of a builder, foam inhibitor, salt, bleach activator, optical brightener, antiredeposition agent, solubilizer, enzyme, thickener, preservative, perfume, dye, pearlizing agent emulsifiers, superfatting agent, biogenic active ingredient and sequestering agent.

2. A detergent, cleaning composition or disinfectant as claimed in claim 1, which comprises from 0.2 to 20% by weight, of said fatty acid alkyl ester ethoxylate.

3. The detergent, cleaning composition or disinfectant as claimed in claim 2, which comprises from 0.5 to 10% by weight, of said fatty acid alkyl ester ethoxylate.

4. A detergent, cleaning composition or disinfectant comprising a chlorine-active substance, a fatty acid alkyl ester ethoxylate of formula $$RO(CH_2CH_2O)_nCOR^1$$

in which R is $C_1$–$C_4$-alkyl, $R^1$ is $C_5$–$C_{22}$-alkyl or $C_5$–$C_{22}$alkenyl, and n is a number from 1 to 30, and a secondary alkanesulfonate.

* * * * *